(12) United States Patent
Gente et al.

(10) Patent No.: US 9,883,931 B2
(45) Date of Patent: Feb. 6, 2018

(54) DEVICE AND METHOD FOR THE APPLICATION OF LIGHT-CURING COMPOSITES

(71) Applicant: Ivoclar Vivadent AG, Schaan (LI)

(72) Inventors: Michael Gente, Colbe (DE); Simone Dudda, Marburg (DE); Arnd Peschke, Planken (LI); Gottfried Rohner, Altstatten (CH); Ulrich Salz, Lindau (DE); Andreas Facher, Gundetswil (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/428,757

(22) PCT Filed: Sep. 18, 2013

(86) PCT No.: PCT/EP2013/069383
§ 371 (c)(1),
(2) Date: Mar. 17, 2015

(87) PCT Pub. No.: WO2014/044711
PCT Pub. Date: Mar. 27, 2014

(65) Prior Publication Data
US 2015/0230900 A1    Aug. 20, 2015

(30) Foreign Application Priority Data
Sep. 18, 2012  (DE) .................. 10 2012 018 384

(51) Int. Cl.
*A61C 19/00*    (2006.01)
*A61C 13/15*    (2006.01)
(Continued)

(52) U.S. Cl.
CPC .............. *A61C 19/004* (2013.01); *A61B 1/04* (2013.01); *A61B 1/24* (2013.01); *A61B 5/0088* (2013.01);
(Continued)

(58) Field of Classification Search
CPC ........................... A61C 19/003; A61C 19/004
See application file for complete search history.

(56) References Cited

U.S. PATENT DOCUMENTS 6,305,934 B1    10/2001  Hatley
6,312,254 B1 *  11/2001  Friedman ............... A61C 5/062
                                                            433/32
(Continued)

FOREIGN PATENT DOCUMENTS

DE    29517958    * 11/1995
EP    2047819 A1    4/2009

*Primary Examiner* — Ralph Lewis
(74) *Attorney, Agent, or Firm* — Ann M. Knab; Thad McMurray

(57) ABSTRACT

The present invention relates to a device and a method for the application of composites in tooth cavities. The device consists of a spray gun with integrated lighting for light-polymerizable composites, a measuring unit and a control unit. The composites are applied under controlled, precisely dosed exposure to polymerization light. According to the invention, the composite initially runs onto the walls of the cavity or onto previously introduced filling material and then, as a result of the light exposure, is transformed into the gel state. Thus, a large part of the polymerization shrinkage of the composite occurs while the composite is still plastically deformable so that any formation of gaps is compensated by the composite continuing to flow. It is only at this point in time that a sufficiently high dosage of light is applied for complete curing to occur.

34 Claims, 4 Drawing Sheets

(51) Int. Cl.

| | |
|---|---|
| *A61C 1/00* | (2006.01) |
| *A61C 5/04* | (2006.01) |
| *A61B 1/04* | (2006.01) |
| *A61B 1/24* | (2006.01) |
| *A61B 5/00* | (2006.01) |
| *A61C 1/08* | (2006.01) |
| *A61C 1/06* | (2006.01) |

(52) U.S. Cl.
CPC .......... *A61B 5/4839* (2013.01); *A61B 5/7405* (2013.01); *A61C 1/0015* (2013.01); *A61C 1/0046* (2013.01); *A61C 1/06* (2013.01); *A61C 1/088* (2013.01); *A61C 5/045* (2013.01)

(56) References Cited

U.S. PATENT DOCUMENTS

| | | | |
|---|---|---|---|
| 6,960,340 B2 * | 11/2005 | Rowe | A61B 1/00165 424/426 |
| 7,014,462 B1 | 3/2006 | Tilse | |
| 2002/0186558 A1 | 12/2002 | Plank et al. | |
| 2005/0048436 A1 | 3/2005 | Fishman et al. | |
| 2007/0118144 A1 | 5/2007 | Truckai et al. | |
| 2010/0249793 A1 | 9/2010 | Truckai et al. | |
| 2010/0304322 A1 * | 12/2010 | Emde | A61C 1/07 433/25 |

\* cited by examiner

DEVICE AND METHOD FOR THE APPLICATION OF LIGHT-CURING COMPOSITES

CROSS-REFERENCE TO RELATED APPLICATIONS

This application is a National Stage application of International patent application PCT/EP2013/069383 filed on Sep. 18, 2013, which claims priority to German patent application No. 2012018384.4 filed on Sep. 18, 2012, the disclosures of which are incorporated herein by reference in their entirety.

TECHNICAL FIELD

The present invention relates to a composite application device for the application of flowable light-polymerizable composites.

The present invention relates to a composite application device according to the preamble of claim 1, as well as a method according to the preamble of claim 23.

Definitions and Abbreviations

Polymerization: Conversion of the composite which is still plastic or flowable into a solid state in which it can withstand occlusal loads.

Carpule: Off-the-shelf container filled with composite material from which the composite material can be expressed using a piston. The carpule can be provided with a short or elongated squirting tube 1.

Cavity, tooth cavity: Hollow space in dental technology, in dentures and tooth crowns.

Cavity wall: Tooth structure which confines the hollow space of a cavity.

Composite, filling material, composite material: Material which serves to fill cavities and which seals these cavities tightly and permanently.

Measuring unit: Device for measuring the amount of composite applied per unit of time.

Control unit: Device for controlling the light intensity of the inventive light source depending on the amount of composite applied per unit of time. The control unit processes the data of the measuring unit and controls the light intensity of the light source.

Tensile stress: Mechanical stress which stresses the bonding at the contact surface between the cavity wall and the composite and which can destroy the bonding upon exceeding the strength of the bonding.

BACKGROUND OF THE INVENTION

In restorative and preventive dentistry, filling cavities, dental defects or root canals of teeth is of special importance. Apart from a plurality of different materials (e.g. gutta-percha, amalgam, gold), composites are also used as filling materials. Composites are mixtures of a polymerizable plastic matrix with organic and inorganic filling materials. The polymerization of these composites is triggered by exposure to visible blue or ultraviolet light after the composites have been applied into the cavity. Thus, the method which is currently common is comprised of first applying the composite into the cavity and subsequently hardening the composite by exposure to light.

All composites tend to form gaps due to their shrinkage behavior during hardening such that in case of the formation of a gap the tooth cavity will not be hermetically sealed. Due to this lack of hermetic sealing of the tooth cavity bacterial infestation of the gaps is possible and thus new caries and pain can be caused.

STATE OF THE ART

The disadvantage of all known light-polymerizable composites is that they shrink upon hardening. If the composites are adhered to the walls of the cavity, then this bonding is subjected to tensile stress after the hardening process. If this tensile stress is sufficiently large to exceed the strength of the bonding, the bonding will break and a gap will be formed between the filling and the tooth.

There are two basic approaches to reduce the shrinkage of the applied composite during and after the hardening process: On the one hand, by applying the composite more slowly and in layers, and on the other hand, by changing the chemical composition of the composite. Both approaches have significant disadvantages: A known process of reducing tensile stresses acting on light-polymerizable composites is to introduce the composites into the cavity which needs to be filled one after the other in small amounts (having a layer thickness of about 1.0 to 2.0 mm), and to harden every layer separately by light exposure.

Every new layer can only be applied when the previous layer has hardened. This process is very labor-intensive and time-consuming. The patient concerned has to hold out on the dental chair in an uncomfortable position and a bacterial contamination of the cavity that has not yet been filled to completion is the more likely, the longer it takes to fill the cavity.

By the use of particularly light-sensitive and translucent composites, layer thicknesses of up to 4.0 mm are possible. This means that the cavity can be filled more rapidly; however, the larger the layer thickness is, the larger the stresses will become during hardening.

In the second approach to reduce shrinkage during or after the hardening of the applied composite, the number or density of the new bonds between the monomer molecules which are formed during polymerization is reduced such that altogether polymerization shrinkage is reduced. However, this method has the substantial disadvantage of a considerably reduced strength of the composite due to the reduced number of chemical bonds.

Another solution comprises the opening of bonds of ring molecules during the polymerization reaction in addition to the formation of new bonds such that in addition to the shrinkage as a result of the polymerization, an expansion of the composite takes place, too, which makes possible to partially compensate for the shrinkage. These composites which have been chemically changed have the disadvantage of only being capable of being bonded to the wall of the cavity using particular adhesion agents, and this is why they have not become established.

From DE 295 17 958 U1 it is known to cure a radiation curable material using a curing lamp which is connected to the opening of the dispensing nozzle. This device is said to have the advantage of curing the exact location at which the dispensing nozzle dispenses the material. Here, the material is cured in one go, i.e. completely, and the same problems as mentioned earlier with regard to the formation of marginal gaps will arise.

Furthermore, it has already been suggested to use an optically opaque, tubular dispensing element for an application tip for the application of a light-curable material to the surface of a tooth, as well as a modeling section which is translucent and disc-shaped in this case, and to expose it to light during the application. This solution takes the beginning of the light curing closer to the surface of a tooth which is basically favorable. However, the quality of the application is highly dependent on the ability of the dentist or dental technician applying the material and on the guidance of the tool. If, for instance, the tool is pressed against the cavity too strongly, the mass to be polymerized is squeezed out to the side of the application area, and if the pressure is too low, fissures and the like will not be filled with material.

In addition, with regard to the formation of marginal gaps the above mentioned disadvantages arise as a result.

SUMMARY OF THE INVENTION

The task of the present invention is to provide a device and a method for the application of flowable light-polymerizable composites, which enable a time-saving processing of light-polymerizable composites and reliably prevent the formation of gaps of the composite during the polymerization process for the filling of cavities.

This task is inventively solved by the appended claims.

Extensive studies on the origins of stresses during the hardening process of composites have found that a large part of the shrinkage which is mainly responsible for the formation of stresses takes place before the composite has hardened completely. The polymerization of the composite turns the composite that has initially been plastic or flowable into a composite with a slightly deformable gel-like consistency, the so-called gel phase. This part of the shrinkage does not become effective in the filling of a cavity built up of thin layers, as in the polymerization of a thin layer the entire filling is initially transformed into the gel phase, which cannot build up stresses on its own and only then is fully polymerized.

The second part of the shrinkage, the so-called post-gel shrinkage, occurs when the composite has already been polymerized, and constitutes the smaller part of the entire shrinkage. This part of the shrinkage cannot be avoided, and therefore always contributes to the formation of stresses. For thick layers, i.e. when the composite is applied in one go in a conventional manner, gel and post-gel shrinkage occurs simultaneously:

While the top side of the thick layer facing the polymerization lamp has already been polymerized completely, a subjacent layer is only in the gel phase due to the light absorption of the composite. Since the surface of the thick layer has already been polymerized, composite material cannot be replenished from above and compensate for the shrinkage of the gel phase: This causes high shrinkage stresses as the shrinkages of the gel phase and the post-gel phase are accumulated.

Thus, in the method according to the invention, sufficient light is supplied during the application of the composite into the cavity such that the composite flows to the walls of the cavity and the gel shrinkage is triggered immediately afterwards so that the gel shrinkage has already taken place, before the composite has been polymerized to completion by a polymerization lamp. It is especially favorable to control the light intensity already during the application of the composite such that when the composite is applied more rapidly (i.e.when larger amounts of composite are applied per unit of time) the light intensity is enhanced, and when the composite is applied more slowly (i.e. when smaller amounts of composite are applied per unit of time) the light intensity is reduced.

Preferably, the inventive device consists of a combination of a spray gun or any other composite application device which serves to squeeze the composite from a suitable storage container, e.g. a commercially available carpule (preferably through the squirting tube of the carpule), and a suitable light source, for instance a light-emitting diode. The light source has to have a suitable light intensity and spectral distribution of the light wave length which is suitable to trigger the first phase of the polymerization of the composite (and thus the gel shrinkage of the composite), while the composite is applied into the cavity simultaneously. By means of a suitable device (the inventive measuring unit), the amount of the composite applied per unit of time is measured and transferred to the inventive control unit as a measured value.

The control unit uses said measured value to control the light intensity of the light source. A potentiometer is preferably used as a measuring unit, especially preferably a sliding potentiometer. The inventive light source emits light while the cavity is filled with composite depending on the amount of the composite applied per unit of time. In addition, the inventive light source can continue to emit light even after the cavity has been filled with composite in order to achieve the final strength of the composite.

While the cavity is filled with composite material, the inventive light source can advantageously emit light colors which do not contribute to a polymerization of the composite. Preferably, light colors are used which can be perceived by the human eye and which enable the treating person (dentist) to gain a better overview of the treatment site (cavity, tooth and its environment). Advantageously, these light colors can be switched on and off independently of the application of the composite.

The light source can be supplied with electricity by one or several batteries or accumulator batteries or by connecting the inventive device with the grid. The inventive application of the composite requires the composite to be flowable to a certain degree in an unexposed state such that when the cavity if filled with the composite, the composite contacts the walls of the cavity and thus bonds to the tooth structure.

For composites which are very viscous in the unexposed state and can thus not meet these requirements it is advantageous to vibrate the carpule or the squirting tube of the carpule 1 or the composite itself using a suitable sound generator in order to liquefy the composite. Depending on the material of the carpule or the squirting tube 1 of the carpule and depending on the composite used audible sound or even ultrasound vibrations can be used.

According to the invention it is favorable that the fluid composite which has been applied or introduced by the application device and which still comprises numerous monomers and free radicals in this state has a relatively low viscosity and can drop into the cavity in this state and forms a thin layer. Due to the thinness, i.e. a state in which the fluid has a very low viscosity, preferably between 1.0 and 1.8 cPs, the composite will also fill small cracks and gaps in the cavity.

After completion of the pre-gel phase, the composite has a tensile bending strength or bending strength of about 20 MPa in the gel state, a strength gradient being present between the surface of the corresponding layer and its deeper regions. For instance, the strength at the surface of a 2 mm layer can be 30 MPa and only 10 MPa at a depth of 2 mm.

According to the invention, it is taken advantage of this strength gradient by applying pressure with the regions of lower viscosity in order to refill gaps and fissures in the cavity—be it with the help of the tool tip of the application device, or with the help of the subsequent layer.

After the composite has been polymerized to completion, it still achieves a final strength of 90 to 100 MPa, and thus fulfills the EN ISO 4049 requirements for occlusal stress bearing regions, too.

According to the invention, it is also favorable for transforming the composite into the gel state if the control device determines a dosage of light which corresponds to a predetermined amount of the dosage of light for a full polymerization of the respective amount of composite, wherein the gelling dosage of light corresponds to 20 to 90, preferably 40 to 65, and in particular about 50 percent of the dosage of light for a full polymerization. The polymerization time per phase, i.e. pre-gel and post-gel phase, amounts to between 1 and 10 seconds, naturally depending on the available power of the light source and the resulting exposure rate, but also on the size and shape of the composite applied per layer.

In the pre-gel phase the exposure rate favorably amounts to less than 100 mW/cm$^2$, in the post-gel phase preferably to more than 500 mW/cm$^2$.

It is especially favorable to alternate the application and polymerization processes, with changes every 10 seconds, every second, or even every 100 msec. This enables a fast application without having to fear the danger of an early polymerization.

For reducing the viscosity of the applied composite a heat source, for instance a heating coil which surrounds a small metallic nozzle pipe, or any other heating, for instance an induction or a microwave heating, is preferably attached to the dispensing nozzle.

According to the invention, the markedly thin composite which preferably comprises microfilled complex materials as a filling material is gelled by the polymerization radiation applied. In said pre-gel phase 90% or up to 95% of the total shrinkage occurs which can amount to 1 to 6% by volume in commercially available composites.

The layer which has been applied can be processed, if necessary, by the dispensing nozzle of the application device which is configured as a tool, for instance in the form of a spatula. This pressure seals the marginal gaps of the composite in the gel state.

According to the invention, pressure is applied to the underlying layer by the composite conitnuing to flow, without even the use of a tool. Once the bottom layer is in the gel state, microscopically small gaps are refilled as a result of this, while at the same time the next layer is gelling and curing simultaneously as the surface stress increases.

Of course, "resqueezing" the composite which continues to flow is preferably carried out with fillings in the lower jaw region, however, in the upper jaw region, too, a recompaction of the material using the dispensing nozzle is detectable.

BRIEF DESCRIPTION OF THE DRAWINGS

Further advantages, details and features may be taken from the following description of several exemplary embodiments in conjunction with the drawings.

DETAILED DESCRIPTION

Figure 1:
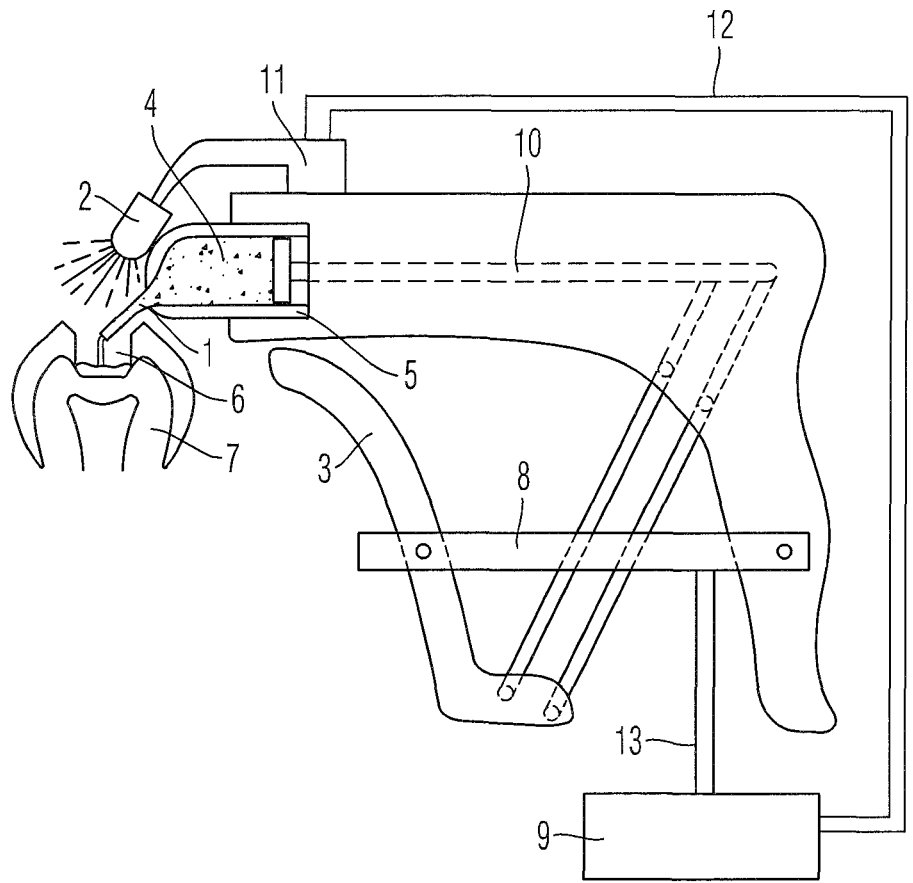
FIG. 1 shows a schematic view of an inventive composite application device.
Figure 2:
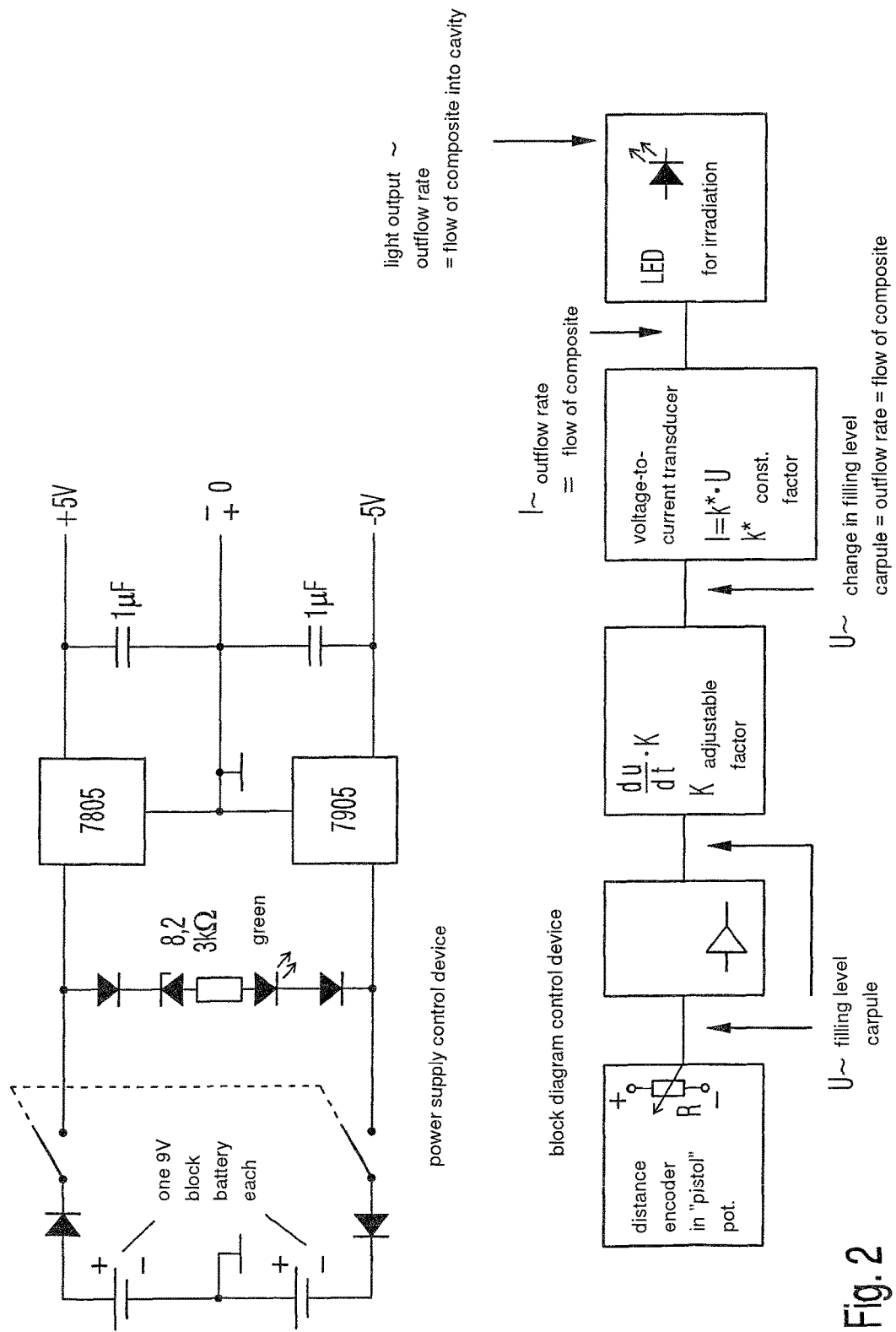
FIG. 2 shows a circuit diagram of a part of the control unit for the composite application device according to FIG. 1, in the form of a block diagram.
Figure 3:
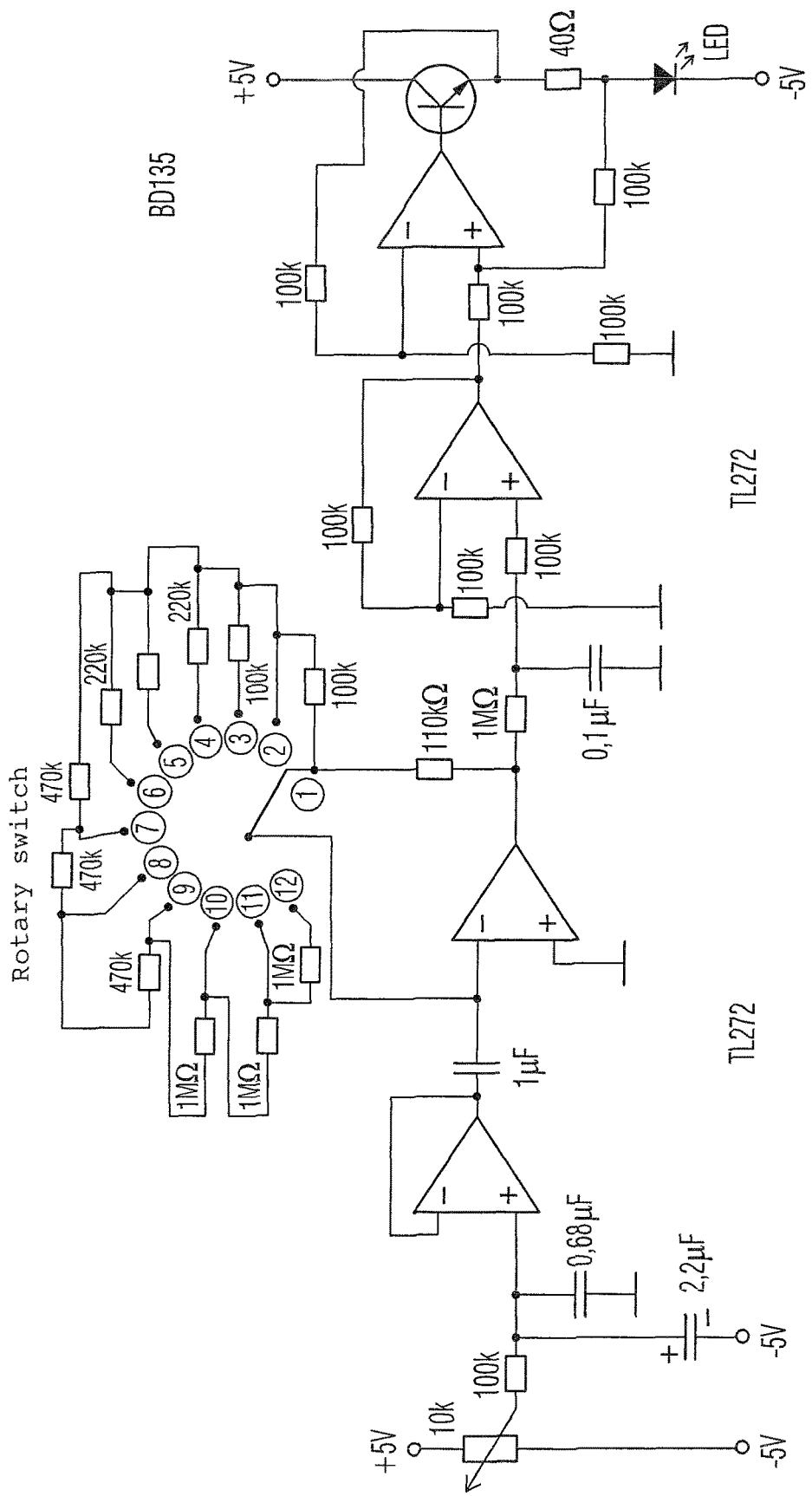
FIG. 3 shows a detailed circuit diagram of the control unit according to FIG. 2.

Close to the squirting tube of the carpule 1 a light source 2, for instance in the form of a light-emitting diode, is attached. The light source may be attached in a fixed or detachable manner. If the light source is attached in a detachable manner, it can be removed for the cleaning of the inventive device. By actuating the lever mechanism 10 of the spray gun 3 the composite 4 is applied from the carpule 5 into the cavity 6 of the concerned tooth (7). In doing so, the measuring unit 8 is activated, for instance by moving the slide of a sliding potentiometer, thus changing the resistance of the potentiometer.

This change is registered in the control unit 9 and converted into a flow of current through the light source 2, in such a way that a larger current is produced when the lever mechanism 10 is moved rapidly than in case of a slow movement of the lever mechanism 10 such that, when the movement is faster, the light source radiates a brighter light into the cavity than in case of a slower movement of the mechanism. An exact dosage of the light dosage is required, depending on the amount of composite applied per unit of time.

If the dosage of light is too high, it prevents the composite from flowing to the cavity wall by immediate gelling, if the dosage of light is too low, however, the gelling process cannot be activated.

It is especially advantageous to measure the amount of composite applied per unit of time in the manner previously described, and to use it to control the light source attached to the spray gun. Here, the light source can be a light-emitting diode which is attached close to the squirting tube of the carpule 1. The light source can also be located at any other desired location at the spray gun and light can be radiated into the cavity by means of a light guide. It is also possible to integrate the light source into the carpule itself or to integrate one or several light guides into the carpule which receive light from the light source and radiate it into the cavity close to the squirting tube. The light source must be provided with contacts or any other suitable optical or electrical connections to the control unit. Lower tensile stresses are produced as follows compared to the conventional layer technique (Table 1).

TABLE 1

| Material | Processing according to manufacturer's instructions (material is applied in one go, subsequently hardened) | Processing in 3 layers (layer or increment technique, every layer is hardened separately) | Processing according to the invention |
| --- | --- | --- | --- |
| SDR (Dentsply Corp.) | 6.3 MPa | 5.2 MPa | 3.3 MPa |
| x-tra base (VOCO Corp.) | 8.9 MPa | 7.3 MPa | 7.0 MPa |

It is especially advantageous that in this type of composite processing the treating person (dentist) can introduce the composite into the cavity in good viewing conditions. While in the layer technique, the field of action must usually only be illuminated sparsely to prevent the composite from polymerizing early, here, a certain amount of light is supplied in a targeted manner such that the composite is transformed into the gel state and cannot flow away anymore. Thus, the light source may also advantageously be configured to not only emit blue light suitable for polymerization but also, for instance, white light with a high blue content, as is emitted by commercially available white light-emitting diodes. In this way it is possible to fill the cavity under good, non-dazzling illumination conditions.

A composite comprising a matrix based on acrylic resins, such as HEMA or TEGDMA, is preferably used. For the inorganic phase, i.e. the filling materials of the composite, glasses such as barium-aluminum-glass, glass ceramics, silicates, or silicon dioxides can be used which comprise both a small amount of macro fillers with a form size of more than 5 mm, but to a large degree micro fillers with a form size of less than 0.2 mm.

According to the invention, the large amount of micro fillers results in a good polishability. While the polymerization shrinkage in composites with a large amount of micro fillers is typically stronger, according to the invention, the formation of marginal gaps is suppressed by the formation of gel during the pre-polymerization process such that the inventively applied composites do not have the same disadvantages as previous composites with a high amount of micro fillers in spite of the extremely smooth surface which is possible in this context.

For instance, the weight portion of micro fillers can amount to 30 to 50% and it is also possible to use nano particles, i.e. fillers with particle sizes of less than 20 nm. By all means, these particles can constitute up to 50% by weight, wherein it is particularly advantageous that the viscosity is not changed by these particles, i.e. remains very low.

According to the invention, it is favorable if the light source 2 is switched on during the application of the composite material. As an alternative, it is also possible to alternate the application of the composite and the polymerization by switching-on the light source 2, for instance with a change in frequency of one Hertz such that composite is applied and the light source is turned on alternately every second.

In this connection, the light source can apply pulsed light, for instance at an impulse/break ratio of 1:1. The output of the light source can be adjusted by pulse width modulation in a way known without any power losses being present.

The composite may, for instance, comprise camphorquinone as a photoinitiator. Preferably, the light source or at least one LED chip of the light source comprises an emission peak of a wave length of approximately 440 nm, and then the main emission range of the LED chips is between 400 and 500 nm.

In an advantageous embodiment the light source 2 comprises at least one LED chip which emits visible light in the range of between 530 and 700 nm and which in this way illuminates the composite when it is applied. It is also possible to switch on the illumination radiation during the application and to switch on the polymerization radiation in application intervals.

It is to be understood that laser diodes can inventively be used as light sources 2 instead of LED chips.

By implementing an additional ultrasonic source in the squirting tube 1 of the carpule the viscosity of the composite can inventively be reduced during the application. Additionally or alternatively, the squirting tube 1 can also be heated in order to further reduce the viscosity and to increase the reactivity of the composite present in monomers. When the composite is heated to, for instance, 30 or 32° C., the double-bond conversion can be increased in the polymerization of the matrix.

In a further advantageous embodiment, the application of the composite is supported by a mechanical drive which can be realized as an electric motor or a pneumatic pressure source. In this embodiment, the control unit 9 controls both the light source 2 and the mechanical drive.

While the invention is described in the context of a spray gun as a preferred embodiment of an application device, it is to be understood that any desired other design of an application device can also be realized. For instance, a stick applicator can also be used, and the light source and the composite source can be configured remote from a handpiece such that the composite is delivered via a composite line to the handpiece of the composite application device and the light via a corresponding light guide.

Initially, a pre-polymerization process takes place in the inventive application or introduction of the composite into the cavity. Here, a particular gelatinizing light dosage is applied which corresponds to between 20 and 80 percent, preferably about 50 percent of the light dosage to completely polymerize the composite. In doing so, the composite gelates, and according to the invention, if desired, finishing can be realized using the dispensing nozzle according to FIG. 4 which is configured similar to a tool. Only then, the final polymerization process takes place.

Thus, the amount of the composite applied is known and the time necessary for the final polymerization can be determined via the energy balance, and applied by the light source —or by the heat source in the squirting tube 1.

It is to be understood that the filling process can inventively be implemented in two steps to form one single layer but it is also possible to repeat the pre-polymerization and final polymerization processes in a cyclical manner for every single layer.

Figure 4A:
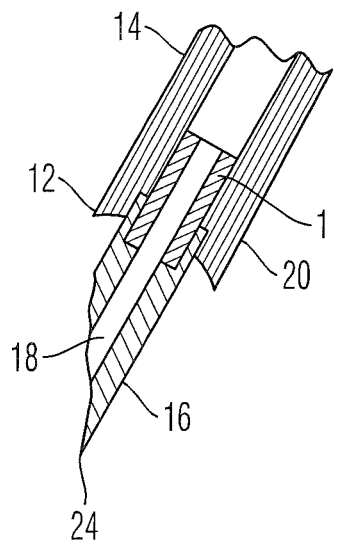
FIG. 4 shows different embodiments of the dispensing nozzle for the composite application device according to FIG. 1 in the embodiments of FIG. 4a, FIG. 4b and FIG. 4c.

FIG. 4a shows one possible shape of an inventive dispensing nozzle 14. In this embodiment, the end of the squirting tube 1 is surrounded by a tool 16. The dispensing channel 18 extends through the tool 16 which channel comprises the same internal diameter as the squirting tube 1, or possibly a tapered cross section towards its end, the shape of which resembles a nozzle.

In the exemplary embodiment illustrated, its end is located at the side of the tool 16. The part of the tool 16 surrounding the squirting tube 1 is further surrounded by an optical system 20 of the source 2. The optical system 20 can be a hollow tube, which is e.g. mirrored on the inside and bundles light towards the tool 16, and thus towards the site of application. It can, however, also be provided with light guides in a way known. Preferably, the end of the optical system 20 is provided with a concave end face 20 which comprises an additional bundling effect.

In this exemplary case, the optical system 20 transmits both light from the LED chips which emit polymerization radiation and light from the LED chips for illumination.

In a way known, the tool 16 is made from an elastic plastic material. With the help of the working tip 24 which is configured similar to a soft spatula the surface of the applied composite can be evened out and pressed which proves advantageous for the adhesion of the composite in the cavity.

Figure 4B:
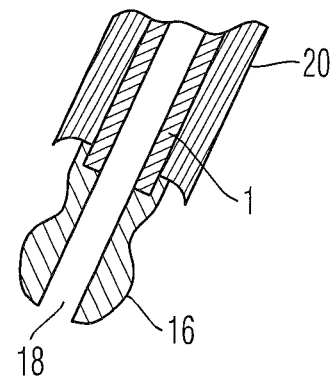

A modified embodiment of the tool 16 is illustrated in FIG. 4b. In this embodiment, the dispensing channel 18 extends through the tool 16 in a central and coaxial manner relative to the squirting tube 1. Here too, the optical system 20 can surround the squirting tube 1 and the upper part of the tool 16. In every case, the tool 16 is preferably an exchangeable tool. It can be configured as a disposable part, or is also cleanable.

Preferably, its upper end is mounted to the squirting tube 1 such that it cannot be lost accidentally.

Figure 4C:
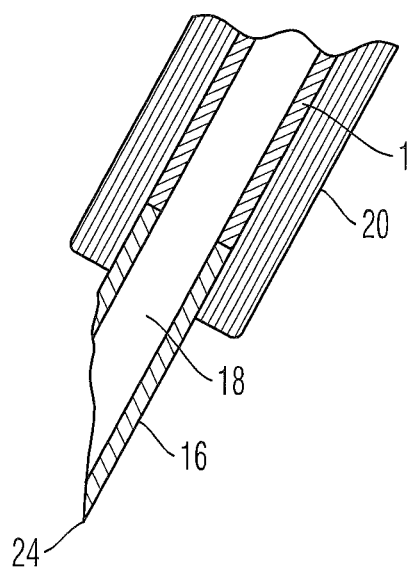

A further modified embodiment of a tool 16 is illustrated in FIG. 4c. Here, the tool 16 is configured so as to be coaxial to the squirting tube 1 and extends in a blunt manner subsequent to the tube. It is held by the surrounding optical system 20, and, in turn, the dispensing channel 18 extends through it which ends at the side of the tool 16 in this exemplary embodiment to provide a very effective tool tip 24.

The invention claimed is:

1. A dental composite application device for the application of flowable light-polymerizable dental composites, the dental device comprising
   a housing,
   a light source which is connected fixedly or detachably to the housing of the dental device and which emits light at least occasionally during the application of the dental composite into a tooth cavity,
   an application element for application of the composite into the tooth cavity,
   characterized in that a detection unit of the dental device detects the amount of composite applied, per unit of time, and
   wherein a control unit controls the light source based on the values obtained by the detection unit such that the composite is transformed into the gel state during the application.

2. The dental composite application device as claimed in claim 1, characterized in that based on the detected amount of the dental composite applied the control unit controls the light source for emitting a dosage of light which corresponds to a pre-polymerization of the composite into the gel state.

3. The dental composite application device as claimed in claim 1 in combination with a dental composite material, characterized in that the dental composite application device can be used with a dental composite having a bending strength of less than 40 MPa in the gel state.

4. The dental composite application device as claimed in claim 3 in combination with the dental composite, characterized in that the bending strength of the dental composite is between 10 and 30 MPa.

5. The dental composite application device as claimed in claim 3, in combination with the dental composite characterized in that the bending strength of the dental composite is approximately 30 MPa.

6. The dental composite application device as claimed in claim 1, characterized in that the control unit controls light exposure of the dental composite into the gel state and stops output of light when the gel state has been reached which corresponds to a predefined dosage of light of the light source relative to the amount of the dental composite applied and signalizes the gel state.

7. The dental composite application device as claimed in claim 1, characterized in that the detection device detects the amount of dental composite to be applied which is leaving the dental composite application device, and in that the control device controls a dosage of light proportional to this amount.

8. The dental composite application device as claimed in claim 1, characterized in that for the conversion of the dental composite into the gel state, wherein the conversion comprises a pre-gel phase, the control device determines an exposure rate and period corresponding to a predefined part of a dosage of light which is necessary to fully polymerize an amount of the dental composite wherein the dosage of light amounts to less than 100 mW/cm$^2$, at a duration of 1 to 10 sec, and wherein the dosage of light amounts to more than 500 mW/cm$^2$ in a post-gel phase.

9. The dental composite application device as claimed in claim 8 in combination with the dental composite, characterized in that the exposure rate and period corresponding to a predefined part of the dosage of light which is necessary to fully polymerize the amount of dental composite in question is about 50 mW/cm$^2$, at a duration of 1 to 10 sec.

10. The dental composite application device as claimed in claim 1, characterized in that the dental composite application device controls the light source in a periodically changing, pulsed, manner, which comprises a higher power during the switch-on time and no power, during the switch-off time.

11. The dental composite application device as claimed in claim 1, characterized in that the dental composite application device dispenses the dental composite in alternation with the emission of light by the light source, changing automatically and periodically at a frequency of changes of between 0.1 Hz and 10 Hz.

12. The dental composite application device as claimed in claim 11, characterized in that the frequency of changes is between about 0.5 to 2 Hz.

13. The dental composite application device as claimed in claim 1, characterized in that the light source comprises at least one laser diode and/or at least one light-emitting diode.

14. The dental composite application device as claimed in claim 13, characterized in that the at least one light-emitting diode comprises a plurality of LED chips arranged in the form of a grid.

15. The dental composite application device as claimed in claim 1, characterized in that the light source emits light in a wave length range which differs from properties of the dental composite comprising a polymerization initiator used for the dental composite having a peak wave length range for initiating curing of the dental composite.

16. The dental composite application device as claimed in claim 15 in combination with the dental composite, characterized in that the difference in wave length of the light from the light source differs from the peak wave length range of the polymerization initiator used for the dental composite by between 530 nm and 700 nm.

17. The dental composite application device as claimed in claim 1 in combination with a dental composite, characterized in that the light source emits light in a pulsed manner in a wave length range, which corresponds to properties of the dental composite comprising a polymerization initiator used having a peak wave length range for initiating curing of the dental composite, and in that beyond this wave length range the light source emits light continuously, in a non-pulsed manner.

18. The dental composite application device as claimed in claim 17, characterized in that the light source emits light in a pulsed manner in the wave length range of 400 nm to 500 nm.

19. The dental composite application device as claimed in claim 1, characterized in that the light source comprises one or more LED chips and at least one LED chip which emits light in a wave length range of between 400 nm and 500 nm can be switched on independently of a further LED chip which emits light in a wave length range of between 530 nm and 700 nm.

20. The dental composite application device as claimed in claim 1, characterized in that the control device increases power of the light source when an amount of dental composite dispensed per unit of time is increased.

21. The dental composite application device as claimed in claim 1, characterized in that the control unit comprises a calibration device which can be used to adjust the relation of light power and flow rate of the composite depending on the composite to be applied, in order to adapt intensity of emission of light to properties of the dental composite.

22. The dental composite application device as claimed in claim 1, characterized in that the dental device signalizes an end of a gelation process of the composite via the dosage of light applied and detected per quantity unit of the composite.

23. The dental composite application device as claimed in claim 1, characterized in that the dental device comprises or is connected to a sound source, the sound source being directed at a dispensing tip of the dental device and/or a cavity and at the composite located at the tip of the dental device and/or the cavity.

24. The dental composite application device as claimed in claim 23, characterized in that the sound source comprises an ultrasonic source.

25. The dental composite application device as claimed in claim 1, characterized in that a heat source for heating the composite during the application, before the gel state is reached, can be switched on, wherein the heat source is attached to a dispensing nozzle.

26. The dental composite application device as claimed in claim 1, characterized in that the dental device can be switched on by means of a switch for emitting light to transform the composite into the gel state and/or for emitting light to reach a completely polymerized state.

27. The dental composite application device as claimed in claim 26, characterized in that the switch comprises a push-button switch or transmitter.

28. The dental composite application device as claimed in claim 1, characterized in that a dispensing tip of the device has a shape of a tool and in that the dental composite in a cavity can be processed directly with the help of the dispensing tip.

29. The dental composite application device as claimed in claim 1, characterized in that a camera or an optical sensor is attached next to or onto a dental composite dispensing tip of the device which optical sensor is directed at the dental composite dispensed and an output signal of which can be supplied to the control unit.

30. The dental composite application device as claimed in claim 1, characterized in that the light source is located near the application element, and electrically connected to the device.

31. The dental composite application device as claimed in claim 1, characterized in that the dental device comprises a pneumatic pressure source or an electric motor for dispensing dental composite.

32. The dental composite application device as claimed in claim 31, characterized in that the mechanical drive comprises an electric motor.

33. The dental composite application device as claimed in claim 1, characterized in that the light source is permanently fixed to the housing of the dental composite application device or is detachable from the housing of the dental composite application device.

34. The dental composite application device as claimed in claim 1, characterized in that the dental device comprises a mechanism for dispensing dental composite.

* * * * *